US012376925B2

(12) United States Patent
Labonville et al.

(10) Patent No.: US 12,376,925 B2
(45) Date of Patent: Aug. 5, 2025

(54) AUTOMATIC MOTION DAMPING OF TELEOPERATED SURGICAL SYSTEM MANIPULATORS

(71) Applicant: Intuitive Surgical Operations, Inc., Sunnyvale, CA (US)

(72) Inventors: Gerard J. Labonville, San Jose, CA (US); Lawton N. Verner, Saratoga, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 312 days.

(21) Appl. No.: 17/976,510

(22) Filed: Oct. 28, 2022

(65) Prior Publication Data

US 2023/0138396 A1    May 4, 2023

Related U.S. Application Data

(60) Provisional application No. 63/273,717, filed on Oct. 29, 2021.

(51) Int. Cl.
| | |
|---|---|
| *H02P 7/281* | (2016.01) |
| *A61B 34/35* | (2016.01) |
| *A61B 34/30* | (2016.01) |

(52) U.S. Cl.
CPC .............. *A61B 34/35* (2016.02); *H02P 7/281* (2013.01); *A61B 2034/305* (2016.02)

(58) Field of Classification Search
CPC .... A61B 34/35; A61B 2034/305; H02P 7/281

(Continued)

(56) References Cited

U.S. PATENT DOCUMENTS

| | | |
|---|---|---|
| 3,628,110 A | 12/1971 | Casaday |
| 3,714,534 A | 1/1973 | Hoadley |
| (Continued) | | |

FOREIGN PATENT DOCUMENTS

| | | | |
|---|---|---|---|
| JP | 2015163031 A | * | 9/2015 |
| JP | 2017100210 A | * | 6/2017 |

OTHER PUBLICATIONS

Srikanth, M.B. et al., "DC Motor Damping: A Strategy to increase Passive Stiffness of Haptic Devices," International Conference on Human Haptic Sensing and Touch Enabled Computer Applications, pp. 53-62, Springer, Berlin, Heidelberg, 2008, 10 pages.

(Continued)

*Primary Examiner* — Jorge L Carrasquillo
(74) *Attorney, Agent, or Firm* — Schwegman, Lundberg & Woessner, P.A.

(57) ABSTRACT

A teleoperated surgical system includes a manipulator, an electric motor, and a power circuit. The motor is operatively connected to and configured to drive movement of at least a portion of the manipulator. The power circuit includes a plurality of wires and a switch. The wires connect a selectively activated power source to the motor. The switch is connected to the wires between the power source and the motor. On a first condition in which the power source changes from an activated state to a deactivated state, the switch short-circuits the motor to cause the unpowered motor to automatically dampen motion of the at least a portion of the manipulator. On a second condition in which the power source changes from the deactivated state to the activated state, the switch electrically connects the motor to the power source to supply operating power from the power source to the motor via the wires.

7 Claims, 8 Drawing Sheets

(58) Field of Classification Search
USPC .................. 318/560, 568.21, 568.11, 568.12
See application file for complete search history.

(56) References Cited

U.S. PATENT DOCUMENTS

| | | | |
|---|---|---|---|
| 7,295,893 B2* | 11/2007 | Sunaoshi | ............... B25J 9/1689 |
| | | | 700/262 |
| 2019/0125388 A1* | 5/2019 | Shelton, IV | ......... A61B 17/105 |

OTHER PUBLICATIONS

Stack Exchange Electrical Engineering thread "Braking a DC brushed motor," Jul. 11, 2011, 5 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

AUTOMATIC MOTION DAMPING OF TELEOPERATED SURGICAL SYSTEM MANIPULATORS

CLAIM OF PRIORITY

This application claims the benefit of priority under 35 U.S.C. § 119(e) to U.S. Provisional Patent Application Ser. No. 63/273,717, filed on Oct. 29, 2021, which is incorporated by reference herein in its entirety.

TECHNICAL FIELD

This document relates generally to medical devices, and more particularly to teleoperated surgical system manipulators.

BACKGROUND

Surgical systems, such as those employed for minimally invasive and orthopedic medical procedures, can include large and complex equipment to precisely control and drive relatively small instruments. Such systems are sometimes referred to as teleoperated systems or robotic surgical systems. One example of a teleoperated surgical system is the da Vinci® surgical system commercialized by Intuitive Surgical, Inc.

Teleoperated surgical systems can control and drive multiple instruments through one or more access ports in the body of the patient. Teleoperated surgical systems can include surgical instrument and user-controlled manipulator systems. The surgical instrument manipulator system can be operated as a follower to the user-controlled master manipulator system. Each of these manipulator systems can include electrically driven (powered) multiple degree-of-freedom (DOF) mechanisms that are configured to articulate in relatively complex motions in three dimensions. For example, a user operates via hands/fingers one or more user-input manipulators, the articulation of which causes articulation of one or more corresponding surgical instrument manipulators.

SUMMARY

Teleoperated surgical system manipulators include at least two links coupled to move with reference to each other at a joint (e.g., rotational, prismatic, spherical, and the like), and they are commonly driven by electric motors connected to actuate motion at joints or other portions of the manipulator mechanism. Such manipulator mechanisms can include low-friction joints, which in the event power is cut to the manipulator mechanism motor(s), may be unconstrained mechanically, electrically, or otherwise. When power is cut to the system, the unconstrained manipulators tend to move without restraint if the overall system/chassis to which they are coupled is moved or otherwise encounters external forces. In such cases, the manipulators or portions thereof can collide with one another or surrounding objects. The inventors have devised a system that short-circuits the manipulator motor when electrical power to the motor is cut, which in effect turns the motor into a generator and causes the motor to automatically dampen motion of the manipulator to which the motor is attached.

Although examples of automatically dampening motion of an electric motor actuated movable component are described in relation to teleoperated surgical systems, examples according to this disclosure could be applied to and employed in other types of systems. For example, automatically dampening motion of an electric motor actuated component by short-circuiting the motor when power to the motor is cut could be employed in a user input device for a video gaming system, e.g. a highly sensitive joy stick, as just one example.

A teleoperated surgical system in accordance with this disclosure includes a manipulator, an electric motor, and a power circuit. The motor is operatively connected to and configured to drive movement of at least a portion of the manipulator. The power circuit includes a plurality of wires and a switch. The wires connect a selectively activated power source to the motor. The switch is connected to the wires between the power source and the motor. On a first condition in which the power source changes from an activated state to a deactivated state, the switch short-circuits the motor to cause the unpowered motor to automatically dampen motion of the at least a portion of the manipulator. On a second condition in which the power source changes from the deactivated state to the activated state, the switch electrically connects the motor to the power source to supply operating power from the power source to the motor via the wires.

A system in accordance with this disclosure includes a movable component, an electric motor, and a power circuit. The electric motor is operatively connected to and configured to drive movement of the movable component. The power circuit includes a plurality of wires and a switch. The plurality of wires electrically connects a selectively activated power source to the motor. The switch is connected to the plurality of wires between the power source and the motor. On a first condition in which the power source changes from an activated state to a deactivated state to cause the motor to be unpowered, the switch short-circuits the motor to cause the unpowered motor to automatically dampen motion of the movable component. On a second condition in which the power source changes from the deactivated state to the activated state, the switch electrically connects the motor to the power source to supply operating power from the power source to the motor via the plurality of wires.

Each of these non-limiting examples can stand on its own or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about various aspects of the inventive subject matter of the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Example teleoperated surgical systems in which examples according to this disclosure may be employed can generally include a user control system and an instrument manipulator system, as well as other components/systems. The user control system of such teleoperated surgical systems can include one or more control input devices, which are contacted and manipulated by the user to control articulation of one or more portions of the instrument manipulator system. Generally speaking, the user can perform surgical tasks at a work site near to or remote from the instrument manipulator system during a surgical procedure by using the control input devices of the user control system to control the instrument manipulator system.

The teleoperated instrument manipulator system can include a plurality of manipulator arms, each coupled to an instrument assembly. An instrument assembly can include, for example, a surgical instrument, and the instrument can include a surgical end effector at its distal end, e.g., for treating tissue of a patient.

The instrument manipulator system can be positioned close to a patient for surgery, where it can remain stationary until a particular surgical procedure or stage of a procedure is completed. The user control system can be positioned in various locations relative to the instrument manipulator system, e.g., in a sterile surgical field close to instrument manipulator system and the work site, in the same room as the instrument manipulator system and work site, or remotely from the instrument manipulator system and work site, e.g., in a different room, building, or other geographic location.

The manipulator arms and instrument assemblies of the instrument manipulator system can be controlled to move and articulate the instruments in response to manipulation by the user of the control input devices of the user control system. For example, when using the user control system, the user can sit in a chair or other support in front of the user control system, position his or her eyes in front of a display unit displaying the surgical site, and grasp and manipulate the control input devices to control surgical instruments connected to manipulators of the manipulator system.

As noted, the instrument manipulator system of such teleoperated surgical systems can include a plurality of manipulators. Additionally, the control input devices manipulated by the user to control the manipulator system can include one or more manipulators. Each manipulator, whether part of a teleoperated surgical system manipulator system or user control system, can include electrically driven multiple DOF mechanisms that are configured to articulate in relatively complex motions in three dimensions.

Figure 1:
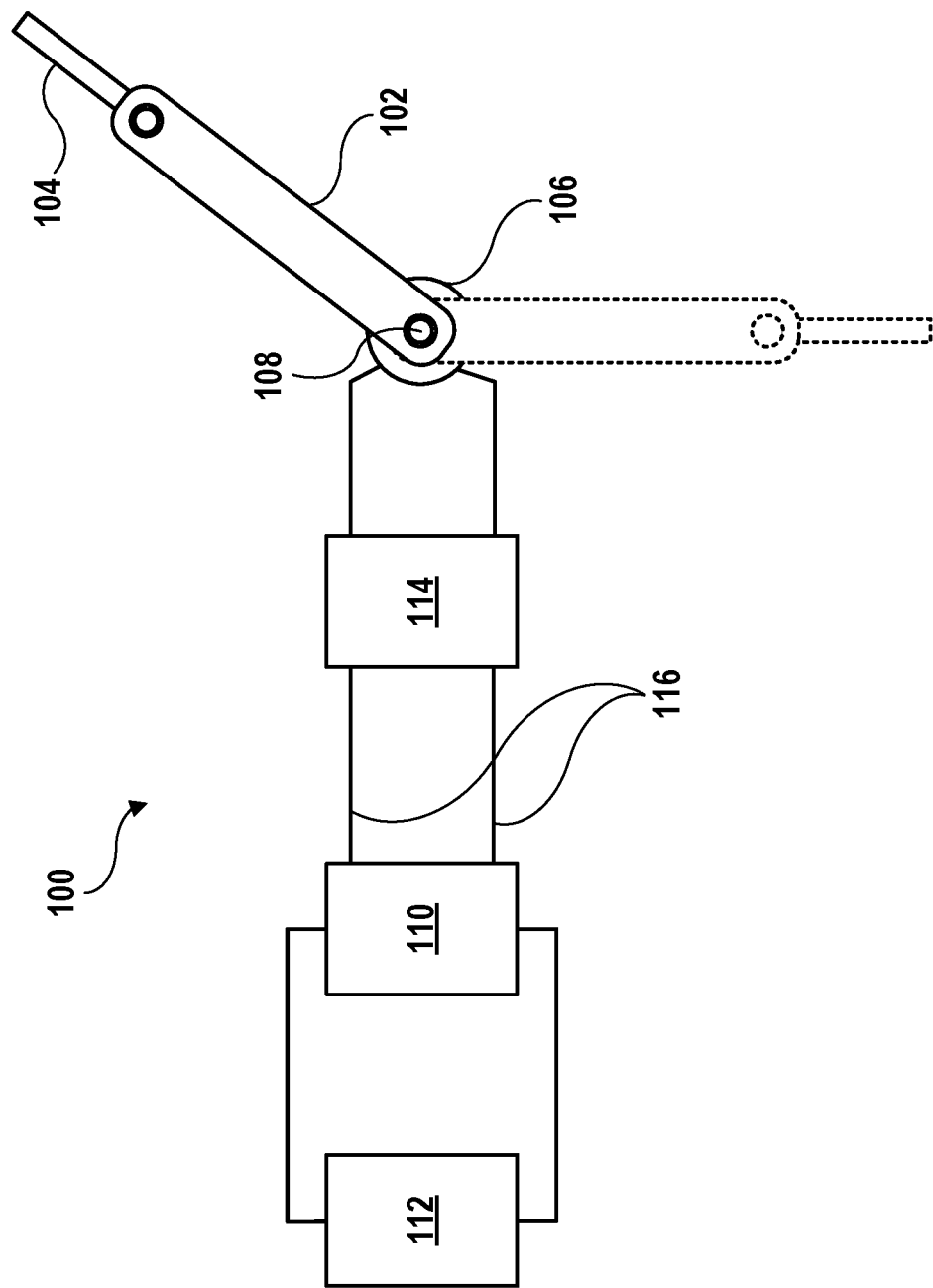
FIG. 1 schematically depicts an example manipulator, which can be a portion of a user control system or a manipulator system of a teleoperated surgical system.

FIG. 1 schematically depicts manipulator 100, which can be a portion of a user control system or an instrument manipulator system of a teleoperated surgical system. In FIG. 1, manipulator 100 includes manipulator arm (a kinematic linkage) 102, end effector 104, motor 106, joint 108, motor driver 110, power source 112, and power circuit 114. Manipulator arm 102 is connected to end effector 104. Manipulator 100 is illustrative of manipulators described herein.

Broadly, end effector 104 represents the distal-most portion of manipulator arm 102. In an instrument manipulator, end effector 104 may be an instrument or a portion of an instrument, or optionally it may be omitted. In a user control system manipulator, end effector 104 is the portion of the manipulator the user grasps so as to move the user control system manipulator.

The motion/articulation of manipulator arm 102 is driven by motor 106, which is connected to manipulator arm 102 at joint 108. In an instrument manipulator, motor 106 moves two or more kinematic links with reference to each other so as to move a surgical instrument coupled to the distal end of the instrument manipulator. In a user control system manipulator, motor 106 likewise moves two or more kinematic links with reference to each other so as to accomplish functions such as initial manipulator arm positioning in space, maintaining manipulator arm position in space against the force of gravity, or providing selected resistance to a user control motion to provide a haptic sensation to the user.

Joint 108 can be a one or more mechanical DOF joint, which is configured to articulate manipulator arm 102 and end effector 104 in one or more dimensions in space. Joint 108 can include a low-friction joint, which in the event power is cut to motor 106, may be unconstrained mechanically, electrically, or otherwise without the advent of examples according to this disclosure. When power is cut to such devices, such unconstrained manipulators can freely swing around if the overall system/chassis to which they are coupled is moved or otherwise encounters external forces. In such cases, a manipulator, or portions of a manipulator, can collide with another manipulator or surrounding objects. The inventors of the subject matter of the present disclosure have therefore devised a system that short-circuits motor 106 when power to the motor is cut, which in effect turns the motor into a generator and causes the motor to automatically dampen any motion of manipulator 102 to which it is attached.

Motor driver 110 is connected to and controls motor 106 via electrical wires 116. Electrical power source 112 is coupled to motor driver 110 and motor 106, and it provides operating power to motor 106. In some examples, motor 106 may be connected to and controlled by a motor driver and/or a motor controller 110. Motor 106 can be connected to one or both of a motor driver and motor controller. A motor driver may be employed to control delivery of the power to motor 106 required for motor operation according to one or more parameters and a motor controller may be employed to control speed, torque, direction (as examples) of the motor.

Power source 112 is an electric power node (e.g., a standard wall plug, a power supply output terminal, a battery, a battery terminal connection, etc.—any electric power node that can transition between powered and unpowered states) that receives generated or stored electrical power (e.g., electrical utility wall power, backup electrical generator power, rechargeable or disposable electrical battery power, etc.) used to run motor 106. Electrical power circuit 114 is connected between motor 106 and power source 112—in this example, between motor 106 and motor driver 110.

In the event power from power source 112 to motor 106 is cut (e.g., changed from an activated state to a deactivated state), power circuit 114 functions to short-circuit motor 106, which in effect turns motor 106 into a generator and causes motor 106 to automatically dampen any motion of manipulator 102. For example, without the function of power circuit 114, in the event power is cut to motor 106, the weight of manipulator 102 would cause manipulator 102 and end effector 104 to fall under the force of gravity, as schematically depicted by the dashed-line position of manipulator 102 and end effector 104 in FIG. 1. In examples according to this disclosure, however, in the event power is cut to motor 106, power circuit 114 functions to cause motor 102 to automatically dampen motion of manipulator 102, which would cause manipulator 102 to maintain the solid-line position depicted in FIG. 1 or to dampen motion of manipulator 102 in a trajectory between the solid and dashed-line positions depicted in FIG. 1. This example is illustrative, and power circuit 114 is configured to cause motor 106 to dampen any motion of manipulator 102, including motion that would otherwise occur when the overall system/chassis to which manipulator 102 is coupled is moved or otherwise encounters external forces.

Figure 2A:
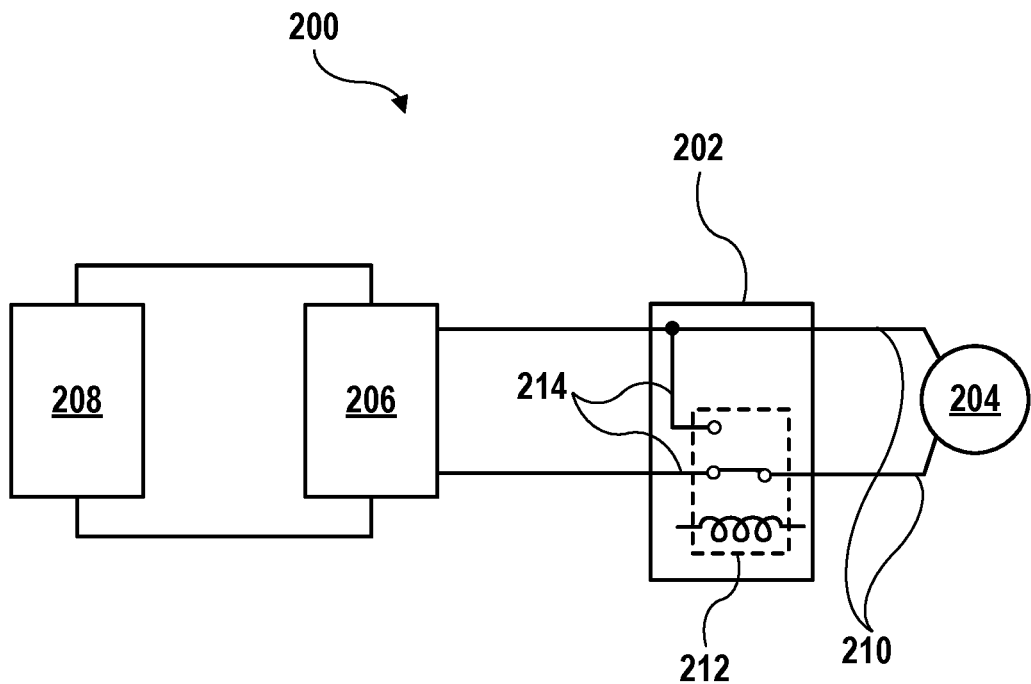
FIG. 2A and FIG. 2B schematically depict another example manipulator including a power circuit in accordance with examples of this disclosure.
Figure 2B:
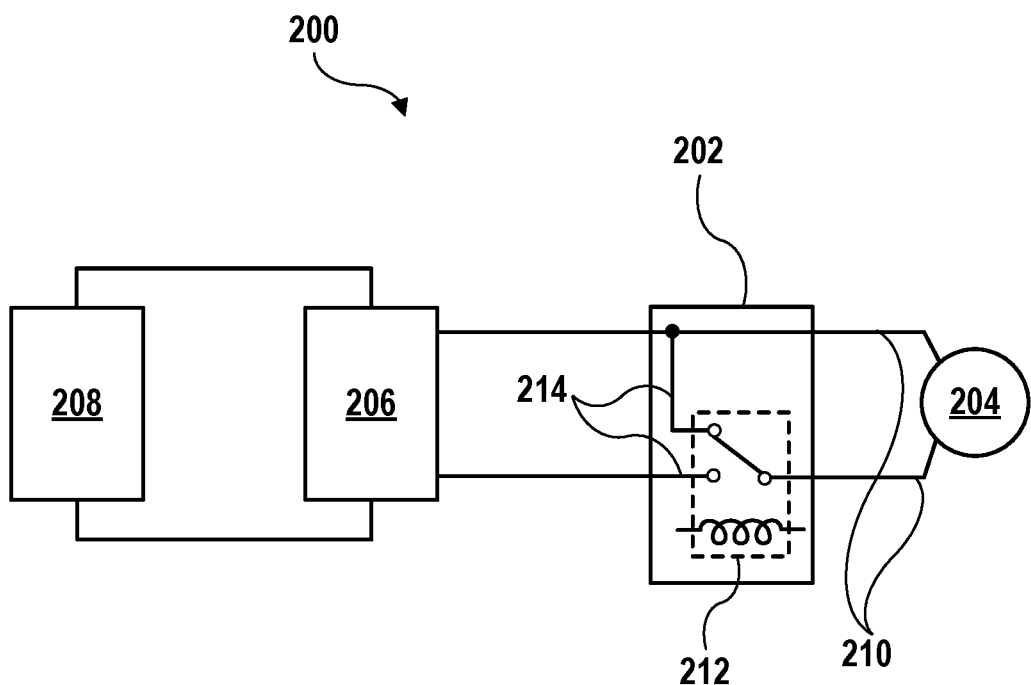

FIG. 2A and FIG. 2B schematically depict another example manipulator 200 including power circuit 202 in accordance with this disclosure. In FIGS. 2A and 2B, manipulator 200 includes electrical power circuit 202, electric motor 204 to which one or more manipulator links are connected (not shown), electric motor driver 206, electric power source 208, and electrically conductive wires 210. Power circuit 202 includes switch 212 and electrically conductive wires 214. In the example of FIGS. 2A and 2B, motor 204 is a brushed motor.

Motor driver 206 is connected to and controls motor 204 via electrical wires 210. Power source 208 is coupled to motor driver 206 and motor 204, and it provides operating power to motor 204. Power source 208 is an electrical power node as described above. Power circuit 202 is connected between motor 204 and power source 208—in this example, between motor 204 and motor driver 206.

Power source 208 is configured to be toggled between an activated state, in which it provides operating power to motor 204 via motor driver 206 and wires 210, and a deactivated state, in which power to motor 204 is cut off. FIG. 2A depicts manipulator 200 in a first state (an activated state), in which power source 208 is supplying operating power to motor 204 via motor driver 206 and wires 210. In this first state, switch 202 of power circuit 202 electrically connects motor 204 to motor driver 206, which is configured to drive and control motor 204 to articulate a manipulator connected to the motor.

FIG. 2B depicts manipulator 200 in a second state (a deactivated state), in which power source 208 is deactivated and power to motor 204 is cut off. In this second state, switch 202 and wires 214 are configured to automatically short-circuit the electrical wires 210 to motor 204 to one another. Short-circuiting motor 204 in the manner depicted in FIG. 2B causes motor 204 to effectively become an electrical generator. In this second state, any motion of the manipulator connected to motor 204 automatically causes motor 204 to generate an electromotive force in the opposite direction of the input motion of the manipulator, which functions to dampen motion of the manipulator.

In the example of FIGS. 2A and 2B, motor 204 is a brushed motor. Additionally, in this example, power circuit 202 functions to short-circuit motor 204 and electrically disconnect motor driver 206. However, additional examples according to this disclosure include power circuits that cause a brushed motor to automatically dampen motion of a manipulator connected to the motor and power circuits that short-circuit the motor and the motor driver to which they are connected.

Figure 3A:
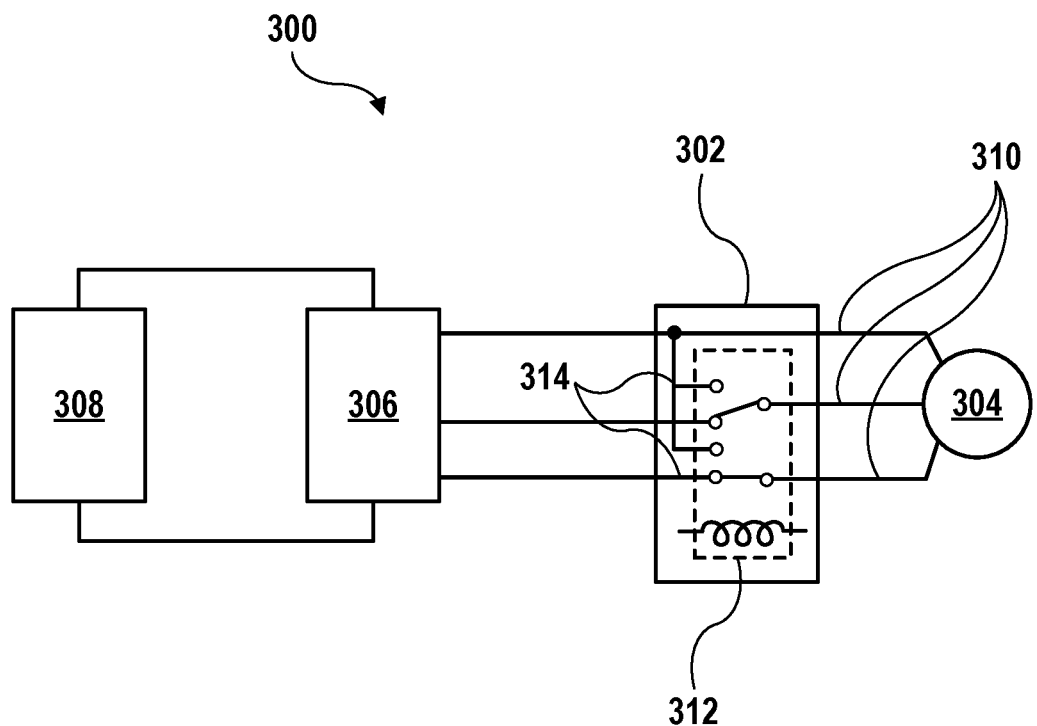
FIG. 3A and FIG. 3B schematically depict another example manipulator including another power circuit in accordance with examples of this disclosure.
Figure 3B:
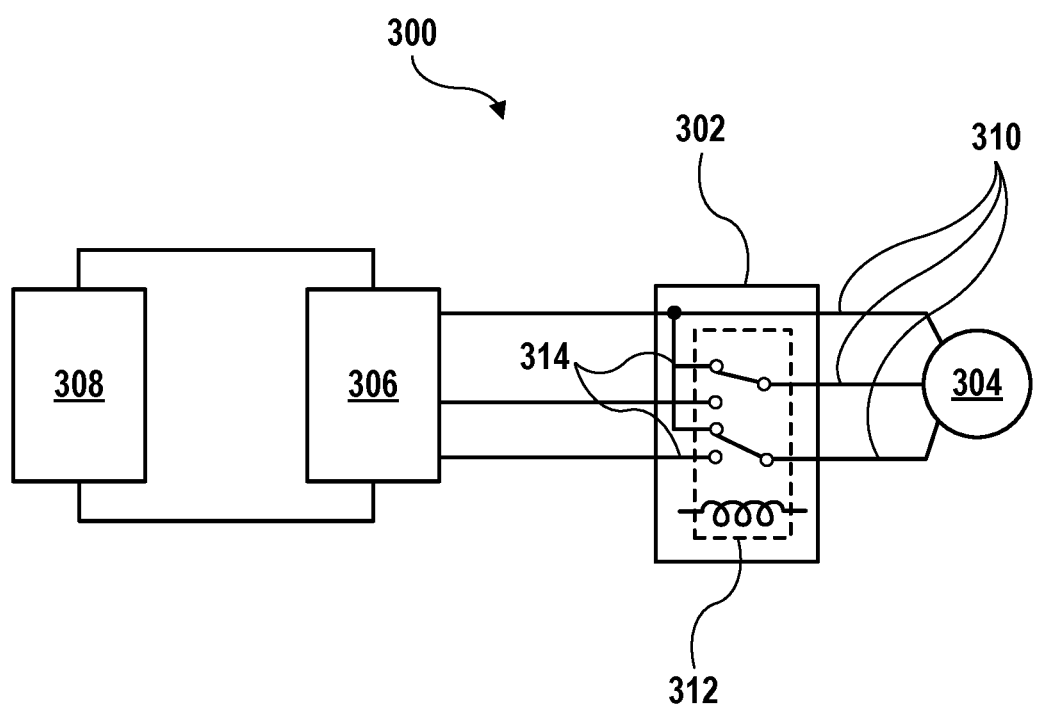

FIG. 3A and FIG. 3B schematically depict another example manipulator 300 including power circuit 302 in accordance with this disclosure. In FIGS. 3A and 3B, manipulator 300 includes electrical power circuit 302, electric motor 304 to which one or more manipulator arm links are connected (not shown), electric motor driver 306, electrical power source 308, and electrically conductive wires 310. Power circuit 302 includes switch 312 and electrically conductive wires 314. In the example of FIGS. 3A and 3B, motor 304 is a brushless motor.

Motor driver 306 is connected to and controls motor 304 via electrical wires 310. Power source 308 is coupled to motor driver 306 and motor 304, and it provides operating power to motor 304. Power source 308 is an electric power node as described above. Power circuit 302 is connected between motor 304 and power source 308—in this example, between motor 304 and motor driver 306.

Power source 308 is configured to be toggled between an activated state, in which it provides operating power to motor 304 via motor driver 306 and wires 310, and a deactivated state, in which power to motor 304 is cut off. FIG. 3A depicts manipulator 300 in a first state (an activated state), in which power source 308 is supplying operating power to motor 304 via motor driver 306 and wires 310. In this first state, switch 302 of power circuit 302 electrically connects motor 304 to motor driver 306, which is configured to drive and control motor 304 to articulate a manipulator connected to the motor.

FIG. 3B depicts manipulator 300 in a second state (a deactivated state), in which power source 308 is deactivated and power to motor 304 is cut off. In this second state, switch 312 and wires 314 are configured to automatically short-circuit the electrical wires 310 to motor 304 to one another. Short-circuiting motor 304 in the manner depicted in FIG. 3B causes motor 304 to effectively become an electrical generator. In this second state, any motion of the manipulator connected to motor 304 automatically causes motor 304 to generate an electromotive force in the opposite direction of the input motion of the manipulator, which functions to dampen motion of the manipulator. Additionally, in the second state depicted in FIG. 3B, in which power source 308 is deactivated, power circuit 302 functions to disconnect motor driver 306 from motor 304.

Figure 4A:
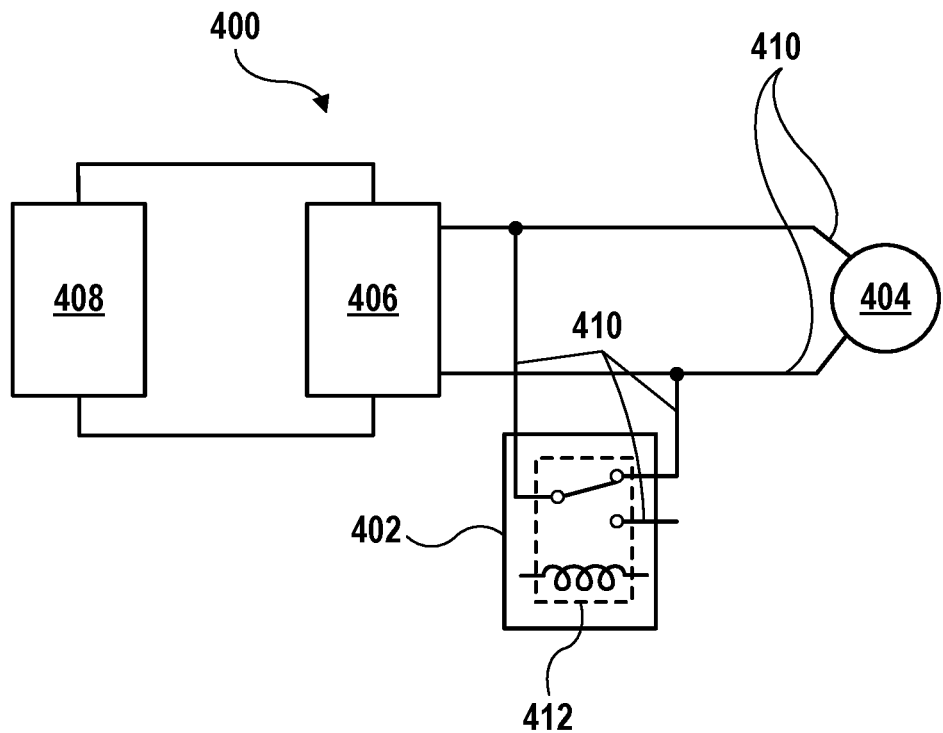
FIG. 4A and FIG. 4B schematically depict two additional example manipulators, respectively including example power circuits in accordance with examples of this disclosure.
Figure 4B:
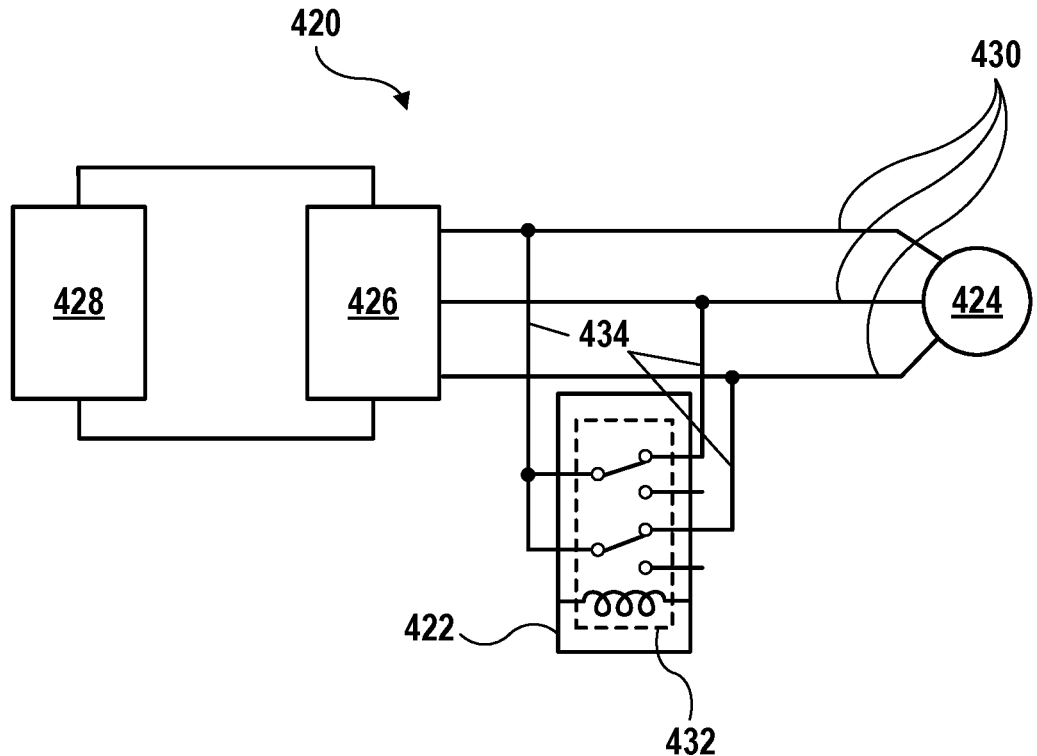

FIG. 4A and FIG. 4B schematically depict two additional example manipulators 400 and 420 in accordance with this disclosure. Referring to FIGS. 4A and 4B, manipulator 400 includes power circuit 402, and manipulator 420 includes power circuit 422. In a similar fashion as described above with reference to FIGS. 2A-2B and 3A-3B, in the examples of FIGS. 4A and 4B, power circuit 402 automatically dampens motion of a manipulator arm connected to brushed motor 404 upon power to motor 404 from power source 408 being cut. Likewise, power circuit 422 automatically dampens motion of a manipulator arm connected to brushless motor 424 upon power to motor 424 from power source 428 being cut. In the example of FIG. 4A, however, in the event power source 408 is deactivated, power circuit 402 also short-circuits motor driver 406. Similarly, in the event power source 428 is deactivated, power circuit 422 also short-circuits motor driver 426.

There are advantages to both example manipulators in which a power circuit short-circuits both the motor and motor driver without physically disconnecting the motor driver, and example manipulators in which a power circuit short-circuits the motor and physically disconnects the motor driver without short-circuiting the motor driver. For example, if the power circuit short-circuits both the motor and the motor driver, the overall manipulator may be more reliable because the electrical circuitry never physically disconnects the motor driver. In examples in which the power circuit short-circuits the motor and physically disconnects the motor driver, if electrical relay or other electrical contacts in the switch of the power circuit degrade to the point they can no longer establish an electrical connection, the motor driver may become disconnected regardless of the activation state of the power source. On the other hand, in examples in which the power circuit short-circuits both the motor and the motor driver, if the switch of the power circuit becomes de-energized while the motor is running, the short-circuited motor driver could damage the driver.

As described with reference to the examples of FIGS. 2A-4B, example power circuits in accordance with this disclosure include a switch. The switch employed in example power circuits is configured to automatically toggle between two states corresponding to corresponding two states of a power source to which the switches are connected. In a first state, in which the power source is activated, the switch of a power circuit in accordance with this disclosure is configured to electrically connect a motor connected to a teleoperated surgical system manipulator to the power source to provide operating power to the motor to articulate the manipulator. In a second state, in which the power source is deactivated, the switch is configured to automatically short-circuit the motor upon deactivation of the power source. A variety of types of switches can be employed in example power circuits 202, 302, 402, 422, and other power circuits in accordance with this disclosure, including a variety of electrically activated switches. For example, switches employed in example power circuits 202, 302, 402, 422, and other power circuits in accordance with this disclosure can include electromechanical relays or solid-state relays or other switching devices including solid-state electronics, as some examples of the types of switching hardware that could be employed in example power circuits in accordance with this disclosure.

The location and packaging of example power circuits in accordance with this disclosure can vary from the particular examples described above with reference to FIGS. 2A-4B. For example, a power circuit that functions to short-circuit a manipulator motor automatically upon the main power (i.e., a main generated or stored electrical power source; in contrast to an auxiliary or backup generated or stored electrical power source) to the motor being deactivated could be incorporated and included in circuitry within a motor driver. As an example, a motor driver commonly includes circuits including field-effector transistors (FETs) that can be controlled rapidly to make and break electrical connections. Such FETs within a motor driver could be controlled to short-circuit the motor within the driver. However, the FETs inside the motor driver would generally be powered by the main power source to the driver and motor, and FET's default state in the absence of power is disconnected. Thus, in such examples, a battery power source could be included in the motor driver. The battery could be connected to FETs of the motor driver such that, upon the main power source to the driver and motor being deactivated, the battery power source is activated to power the FETs in the motor driver to short-circuit the motor.

Figure 5A:
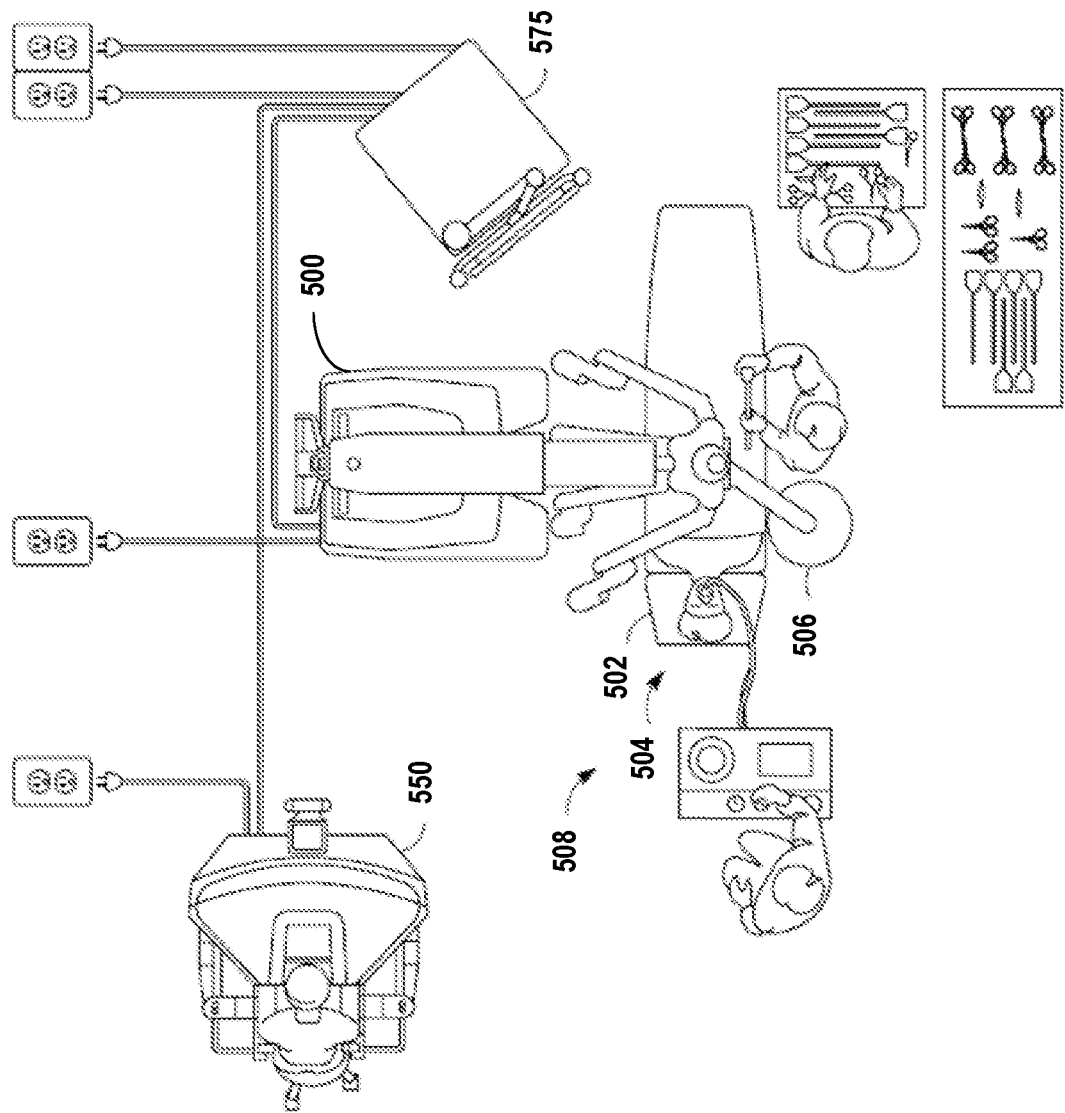
FIG. 5A is a plan view depicting an example teleoperated surgical system in a surgical environment.

FIG. 5A is a plan view depicting an example medical procedure environment that includes a multi-arm manipulator system 500 adjacent to a surgical table 502 that supports a patient 504. In FIG. 5A, a second manipulator system 506 may also be situated at the surgical table 502. The manipulator systems 500, 506 may be free-standing on a movable base, or they may be mounted to a table, floor, wall, or ceiling, or they may be supported on another piece of equipment in the clinical environment.

The manipulator system 500 or system 506 may be part of a larger system 508, which may include other sub-systems, including, for example, fluoroscopy or other imaging equipment. One or both of the manipulator systems 500, 506 may be operatively coupled to a user control system 550. The user control system 550 may include one or more user input devices (e.g., controls) that may be configured to receive inputs from a user (e.g., clinician). The user control system 550 may also include or one or more user feedback devices (e.g., viewing system, or tactile or auditory feedback system) that may be configured to provide information to the user regarding the movement or position of an end effector, or an image of a surgical area. Example power circuits in accordance with this disclosure, which function to cause a manipulator motor to automatically dampen motion of the manipulator connected to the motor upon power to the motor being cut can be employed in, for example, manipulator system 500, manipulator system 506, and/or user control system 550.

Figure 5B:
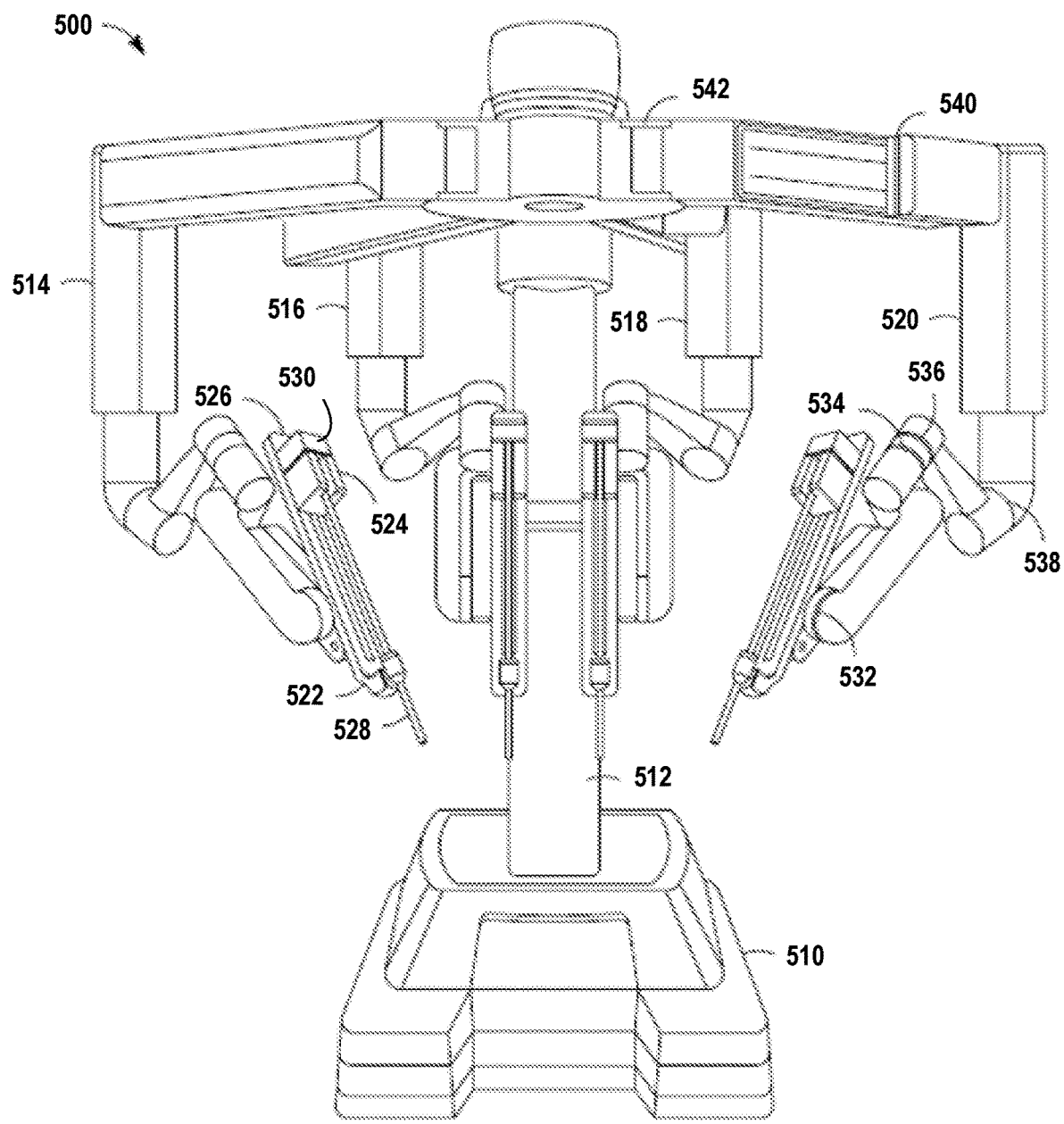
FIG. 5B depicts an example teleoperated manipulator system.

FIG. 5B depicts example manipulator system 500. The example manipulator system 500 includes a base 510, a support tower 512, and one or more manipulator arms 514, 516, 518, 520, which may be mounted on the support tower 512. An instrument 530 (shown in more detail in FIG. 5D) is mounted to an instrument mount 522 on one of the manipulator arms 514, 516, 518, 520. The instrument mount 522 includes, as an example, an instrument carriage 524, which is mounted to a spar 526, which may be a telescoping or non-telescoping spar. A cannula 528 may be mounted to a cannula mount 526, and the instrument 530 may be inserted through a cannula seal in the cannula 528, and into the patient 504 (FIG. 5A) for use in a therapeutic or diagnostic surgical procedure. Through movement of the manipulator arms 514, 516, 518, 520, the translation and orientation of the instrument 530 may be controlled in multiple mechanical degrees of freedom, e.g. lateral, horizontal, vertical, angular movements in one, two, or three planes.

The translation and change in orientation of instrument 530 via manipulator arms 514, 516, 518, 520 may be driven by one or more electric motors, e.g. motors connected to and driving joints of the manipulator arms. In examples according to this disclosure, a power circuit may be connected between such manipulator motors and the power source powering the motors. Such power circuits, as described with reference to the examples of FIGS. 1-4B, can function to short-circuit the motor in the event power is cut thereto, which, causes the motor to automatically dampen motion of the manipulator.

Figure 5C:
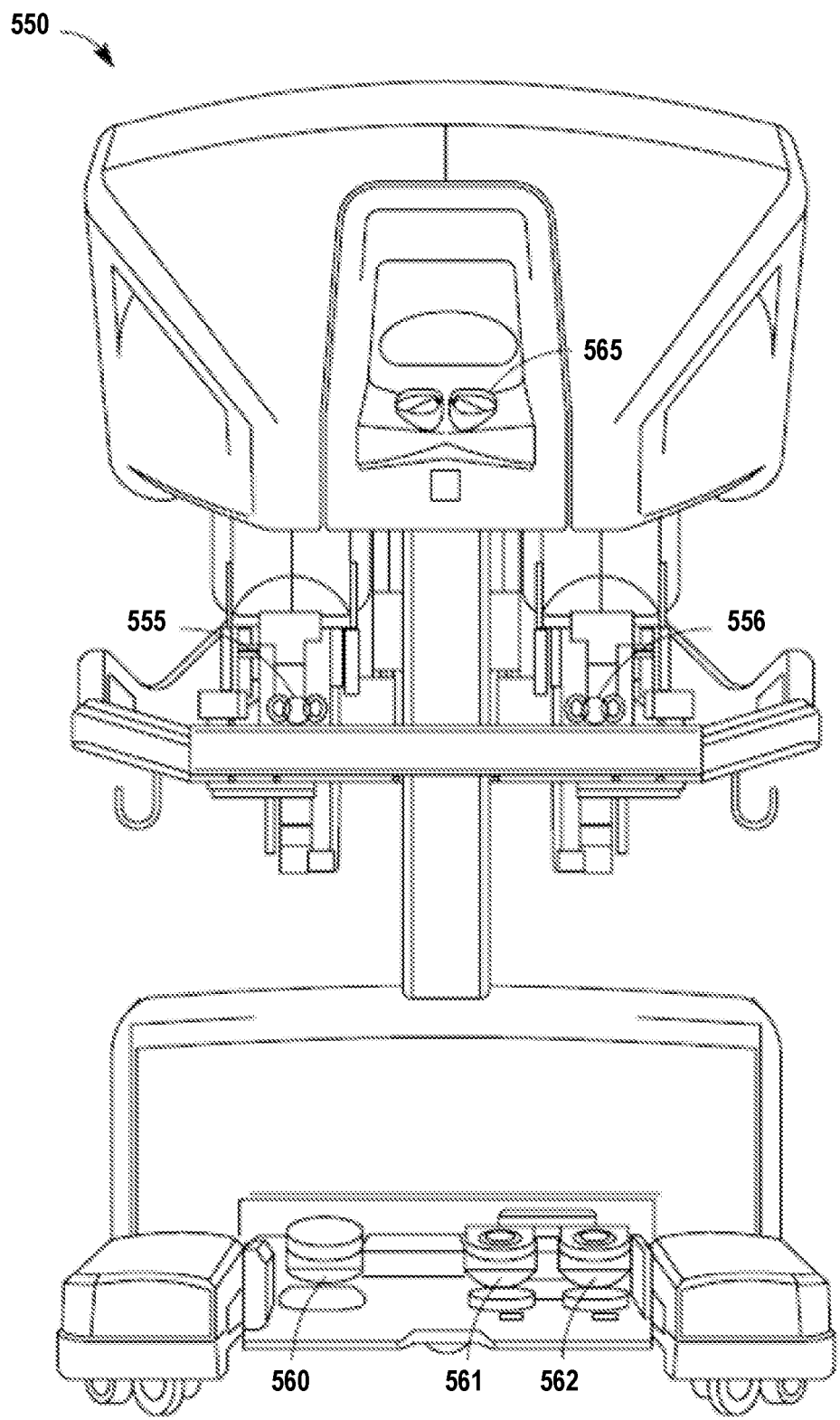
FIG. 5C depicts an example user control system.

FIG. 5C depicts example user control system 550. The user control system 550 includes hand controls 555, 556 and foot pedal controls 560, 561, 562. The hand controls 555, 556 and foot pedal controls 560, 561, 562 are used to control equipment at one or more of the manipulator systems 500, 506. For example, an operator may manipulate portions of a distal end of an instrument 530 by using the instrument controls. The controls may include haptic feedback features so that a surgeon may interpret physical information at the instrument 530, such as resistance or vibration, through the controls. The user control system 550 may also include a viewing system 565 that displays video or other images of a surgical site.

The control input devices of user control system 550, e.g., hand controls 555, 556 can include one or more manipulators, which may be driven by an electric motor. In a similar fashion as described with reference to the manipulators of manipulator system 500, manipulators of user control system 550 can include a power circuit connected between manipulator motor and a power source powering the motor. Such an example power circuit can function to short-circuit the motor in the event power is cut thereto, which causes the motor to automatically dampen motion of the manipulator of user control system 550.

Figure 5D:
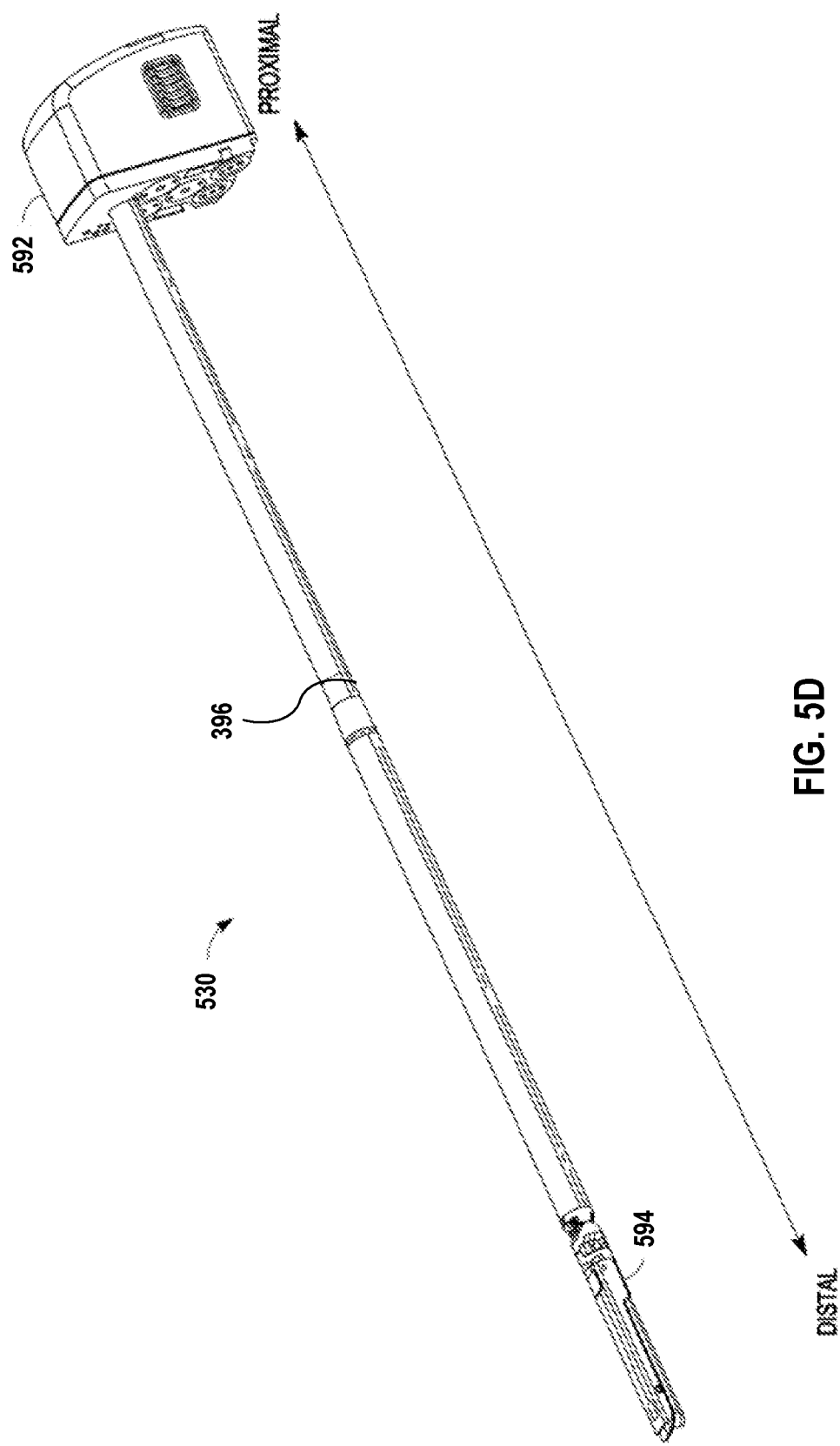
FIG. 5D depicts an example instrument.

FIG. 5D depicts example instrument 530. The instrument 530 includes a proximal portion 592, which is configured to couple to an instrument mount on a manipulator arm. The instrument 530 also includes a distal portion 594 and an instrument shaft 596 between the proximal portion 592 and the distal portion 594. The distal portion 594 shown is a stapler, and in other instruments it may be a cautery tool, cutter, camera, or other medically relevant end effector. The instrument 530 may be teleoperatively controlled via command signals received from a control computer, such as a user control system 550 to conduct a surgical procedure. Inputs may be received from a user (e.g., clinician), and the instrument 530 may be controlled based on the user inputs.

Persons of skill in the art will understand that any of the features described above may be combined with any of the other example features, as long as the features are not mutually exclusive. All possible combinations of features are contemplated, depending on clinical or other design requirements. In addition, if manipulator system units are combined into a single system (e.g., telesurgery system), each individual unit may have the same configuration of features, or, one patient-side unit may have one configuration of features and another patient-side unit may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b) so as to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A teleoperated surgical system comprising:
a manipulator arm including a link;
an electric motor operatively connected to and configured to drive movement of the link of the manipulator arm; and
a power circuit comprising a first plurality of wires and a switch;
a motor driver and a second plurality of wires;
wherein the first plurality of wires electrically connects a selectively activated power source to the motor and the motor driver to the motor, and the second plurality of wires connects the motor driver to the power source;
wherein the switch is connected to the plurality of wires between the power source and the motor;
wherein on a first condition in which the power source changes from an activated state to a deactivated state to cause the motor to be unpowered, the switch short-circuits the motor to cause the unpowered motor to automatically dampen motion of the link of the manipulator arm and short circuits the motor driver; and wherein on a second condition in which the power source changes from the deactivated state to the activated state, the switch electrically connects the motor driver to the motor to the power source to supply operating power from the power source to the motor via the first plurality of wires.

2. The teleoperated surgical system of claim 1, wherein: the motor is a brushless motor.

3. The teleoperated surgical system of claim 1, wherein: the switch includes solid-state electronics.

4. A teleoperated surgical system comprising:
means for constrained movement of a portion of the teleoperated surgical system;
an electric motor operatively connected to and configured to drive movement of the portion of the teleoperated surgical system;
a motor driver;
means for selectively supplying electricity;
means for conducting electricity supplied by the means for selectively supplying electricity; and
means for switching the means for conducting electricity between the means for selectively supplying electricity and the motor;
wherein on a first condition in which the means for selectively supplying electricity changes from an activated state to a deactivated state, the means for switching short-circuits the motor to automatically dampen motion of the at least a portion of the means for constrained movement and short circuits the motor driver; and
wherein on a second condition in which the means for selectively supplying electricity changes from a deactivated state to an activated state, the means for switching electrically connects the motor driver to the motor to the means for selectively supplying electricity to supply operating power from the means for selectively supplying electricity to the motor via the means for conducting electricity.

5. A system comprising:
a movable component;
an electric motor operatively connected to and configured to drive movement of the movable component; and
a power circuit comprising a first plurality of wires and a switch;
a motor driver and a second plurality of wires;
wherein the first plurality of wires electrically connects a selectively activated power source to the motor and the motor driver to the motor, and the second plurality of wires connects the motor driver to the power source;
wherein the switch is connected to the plurality of wires between the power source and the motor;
wherein on a first condition in which the power source changes from an activated state to a deactivated state to cause the motor to be unpowered, the switch short-circuits the motor to cause the unpowered motor to automatically dampen motion of the movable component and short circuits the motor driver; and
wherein on a second condition in which the power source changes from the deactivated state to the activated state, the switch electrically connects the motor to the power source to supply operating power from the power source to the motor via the plurality of wires.

6. The system of claim 5, wherein: the motor is a brushless motor.

7. The system of claim 5, wherein: the switch includes solid-state electronics.

* * * * *